(12) United States Patent
Jacobson et al.

(10) Patent No.: US 10,140,833 B1
(45) Date of Patent: Nov. 27, 2018

(54) FALL PREDICTOR AND NOTIFICATION SYSTEM

(71) Applicant: Bear State Technologies, LLC., North Little Rock, AR (US)

(72) Inventors: Shannon R. Jacobson, North Little Rock, AR (US); Robert Darin Flippo, Conway, AR (US)

(73) Assignee: Bear State Technologies, LLC., North Little Rock, AR (US)

( * ) Notice: Subject to any disclaimer, the term of this patent is extended or adjusted under 35 U.S.C. 154(b) by 0 days.

(21) Appl. No.: 15/353,261

(22) Filed: Nov. 16, 2016

(51) Int. Cl.
*G08B 21/04* (2006.01)
*G08B 23/00* (2006.01)
*A61B 5/11* (2006.01)
*A61B 5/00* (2006.01)

(52) U.S. Cl.
CPC ........ *G08B 21/0446* (2013.01); *A61B 5/0002* (2013.01); *A61B 5/1117* (2013.01); *A61B 5/7275* (2013.01); *A61B 5/744* (2013.01); *A61B 2562/0219* (2013.01)

(58) Field of Classification Search
CPC . G08B 21/0446; A61B 5/0002; A61B 5/1117; A61B 5/7275; A61B 5/774; A61B 2562/0219
See application file for complete search history.

(56) References Cited

U.S. PATENT DOCUMENTS

| 5,315,512 A | 5/1994 | Roth | |
|---|---|---|---|
| 6,433,690 B2 | 8/2002 | Petelenz | |
| 8,023,726 B2 | 9/2011 | Sundaresan | |
| 8,814,811 B2 | 8/2014 | Scholten | |
| 8,990,041 B2 | 3/2015 | Grabiner | |
| 9,041,810 B2 | 5/2015 | Ecker | |
| 2008/0186189 A1* | 8/2008 | Azzaro | ................. A61B 5/1113 340/573.7 |

(Continued)

*Primary Examiner* — Sisay Yacob
(74) *Attorney, Agent, or Firm* — Joe D. Calhoun

(57) ABSTRACT

A system for predicting the fall of a subject's body, displaying the subject's body positioning on a monitor screen in a manner not revealing personal health information or otherwise breaching privacy concerns, and warning assistants when the subject is at risk for an imminent fall. The system includes a sensor assembly having a 3-dimensional 3-axis gyroscope and accelerometer positioned centrally on the subject's body to sense the subject's spatial positioning at short intervals and generate a corresponding sequence of positioning data, that is transmitted wirelessly to a processing assembly. A computer processing unit having associated software programming determines whether the displacement differential between the subject's present positioning and the subject's previous positioning exceeds a threshold predictive of imminent bodily fall, accomplished by comparing the subject's displacement differentials of each axis' sequential positioning data obtained after each of said intervals. A monitoring assembly includes a plurality of monitor screens, each showing a representation reflecting the positioning of at least one of a plurality of subject's bodies according to the current positioning data for the respective subject; the processing assembly activates at least one imminent-fall alarm if the displacement differential of any axis is equal to or larger than an established threshold.

20 Claims, 8 Drawing Sheets

(56) References Cited

U.S. PATENT DOCUMENTS

| | | | |
|---|---|---|---|
| 2009/0322540 A1* | 12/2009 | Richardson | A61B 5/0002 |
| | | | 340/573.7 |
| 2011/0144542 A1* | 6/2011 | Jin | A61B 5/0002 |
| | | | 600/595 |
| 2014/0100487 A1* | 4/2014 | McNair | A61B 5/00 |
| | | | 600/595 |

* cited by examiner

FIG. 8
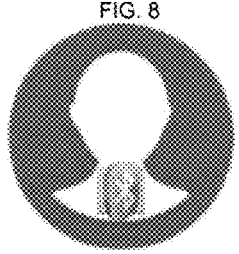
Wireless Device located on Patient
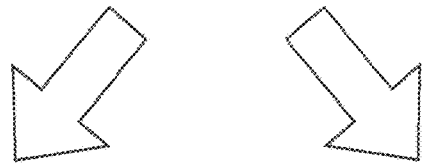
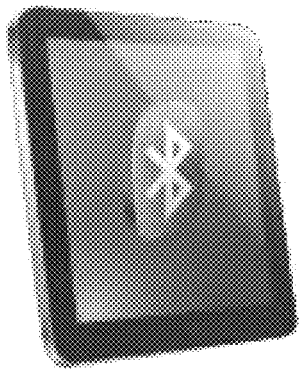
Bluetooth Device directly connects to
Mobile Device with bluetooth capabilities
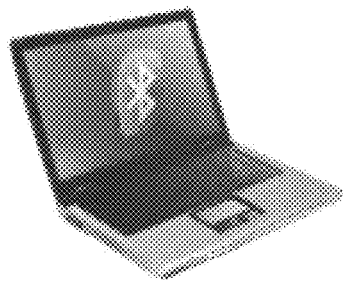
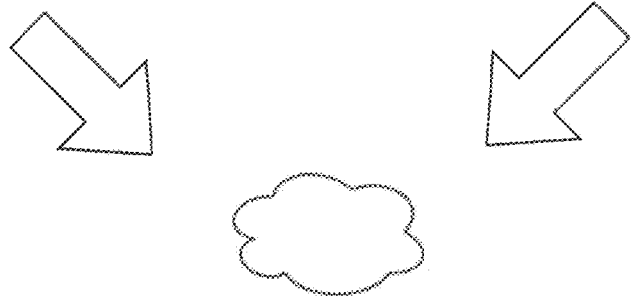
Stores data
for research
and
movement
archival

FALL PREDICTOR AND NOTIFICATION SYSTEM

CROSS REFERENCE TO RELATED APPLICATIONS

Not applicable.

FEDERALLY SPONSORED RESEARCH AND DEVELOPMENT

Not applicable.

MICROFICHE APPENDIX

Not applicable.

BACKGROUND OF THE INVENTION

(1) Field of the Invention

The present disclosure generally relates to systems using a model of the body of a subject (such as a person or vehicle), to portray changes to the subject's bodily orientation and to predict a noteworthy incident based upon bodily movements causing such changes. The invention disclosed herein relates primarily to systems showing a person's bodily positioning, predicting the person's fall based on bodily positioning, and providing a notification of an imminent fall. More particularly, the present invention relates to a system allowing assistants such as caregivers and health care providers to monitor the bodily positioning of a person using a representative model of the person's body that does not show personal health information or otherwise breach privacy regulations or concerns, and alarms the assistant of an imminent fall by the person.

(2) Background of Invention

The invention disclosed here involves the confluence of several previously distinct technologies, but requiring heretofore non-coordinated functionalities. There are some known systems having one or more functionalities of the system disclosed herein, but none include the complete collection of functionalities that have been coordinated to produce the non-obvious synergies of the predictive and privacy functionalities of the invention disclosed herein. The following are examples of such known systems.

U.S. Pat. No. 5,315,512 issued to Roth discloses generating a 3D model of a body/part using an ultrasonic imager and 3D digitizer. The three-dimensional representation of a body can then be animated (changed orientation). This reference does not disclose a system comprising a 3-axis accelerometer sensing the body's orientation. Neither does it determine whether orientational changes manifest an imminent fall and, if so, transmit an alarm to interested caregivers.

U.S. Pat. No. 6,433,690 issued to Petelenz discloses detecting whether a fall is controlled or not, by change in accelerometer data. Although "predicting" a fall is mentioned once, it discloses only detecting falls that have already occurred. This reference does not disclose a system that translates data into a graphical representation of a human body and determines whether orientational changes manifest an imminent fall and, if so, transmits an alarm to interested caregivers.

U.S. Pat. No. 8,023,726 issued to Sundaresan discloses using surrounding cameras to provide data to construct a subject model displayed in a pose, then tracked for re-posing. It discloses an algorithm which builds a 3-D model/pose estimation, and includes pose tracking. Algorithms estimate the complete human body model from all the body parts of a moving human based on input from movements. It discloses some predictive functionality, but only to yield an estimated pose to be corrected with energy image data. This reference does not disclose a system comprising a 3-axis accelerometer sensing the body's orientation. Nor does this system determine whether orientational changes manifest an imminent fall and, if so, transmit an alarm to interested caregivers.

U.S. Pat. No. 8,814,811 issued to Scholten discloses a fall detection system comprising a 3-axis accelerometer worn by a subject, that provides input to a controller comparing a current position vector and a later reference vector, the difference determined by an algorithm to manifest a patient fall. This reference does not disclose a system transmitting sensor data to a central transceiver that translates the data into a graphical representation of a human body and determines whether orientational changes manifest an imminent fall and, if so, transmits an alarm to interested caregivers.

U.S. Pat. No. 8,990,041 issued to Grabiner discloses a 3-axis accelerometer worn by a subject, and a controller analyzing the subject's kinematic data to determine whether a postural disturbance threshold is exceeded, indicative of a fall or an imminent fall. This reference does not disclose a system that translates sensor data into a graphical representation of a human body.

U.S. Pat. No. 9,041,810 issued to Ecker discloses a system for predicting patient falls from patient "movement signatures", the system comprising a camera and chronological or sequential mapping of luminescence/movement across detection fields. This reference does not disclose a system comprising a 3-axis accelerometer sensing the body's orientation and then transmitting such data to a central transceiver that translates the data into a graphical representation of a human body and determines whether orientational changes manifest an imminent fall.

BRIEF SUMMARY OF THE INVENTION

Although the system disclosed herein primarily involves monitoring the positioning of a human body to predict an imminent fall, the system may be adapted to predict the imminent behavior of vehicles or other bodies prior to an occurrence of an incident that may be either desired or undesired. For example, sensors placed on a vehicle (on or off road), or on the driver of such a vehicle, can be used to predict the likelihood of a roll over. The same for boats and capsizing. In any event, although this disclosure will sometimes refer to a patient, it should be construed to apply to subjects involved in other applicable contexts. Similarly, although this disclosure sometimes refers to a caregiver, it should be construed to apply to assistants involved in other applicable contexts. Moreover, despite references to a bodily fall, the predicted outcome should not be so limited, since the predicted outcome may include virtually any movement culminating in a desirable or undesirable conclusion which may be generally known as an incident.

In general, the invention disclosed herein includes (comprises) a system for predicting the fall of a subject's body, including:

(a) a sensor assembly including a sensor positioned on the subject's body to sequentially sense the subject's spatial positioning at short intervals and generate a corresponding sequence of positioning data, operatively coupled to;

(b) a processing assembly sequentially receiving the positioning data and including a computer processing unit having associated software programming for determining whether the difference between the subject's present positioning and the subject's previous positioning exceeds a threshold predictive of imminent bodily fall.

In general, the system disclosed herein uses a pre-made mesh that constructs the 3D model, and then rotates or re-orients that model based on sensed changes in the subject's x, y and z axes in relation to coordinates in space.

The system disclosed herein not only displays the alarm on a monitor, but also may direct the viewer's attention to the subject in need of attention. For example, the portion of the screen for that subject's model may be brightened (or the other portions of the monitor screen dimmed). Alternatively, that model may become centered on the screen and perhaps enlarged (or the other model portions move to the periphery and perhaps made smaller or less distinct. Moreover, the background color of that model may be highlighted.

The system will also store the data, to discern whether the patient's orientation manifests a trend elevating his or her fall risk.

A primary object of the current disclosure is to provide a sensor system that predicts whether a subject is about to fall from an essentially vertical position, or otherwise depart uncontrollably from a resting position of any orientation.

Another object of the current disclosure is to provide a sensor system that displays a subjects bodily positioning on one or more monitor screens, without intruding on the subject's privacy or otherwise revealing personal health information concerning the subject.

Yet another object of the current disclosure is to provide a sensor system that alerts one or more individuals monitoring the subject, that a fall or other incident is imminent.

Yet another object of the current disclosure is to provide a sensor system that gathers data from one or more sensors positioned on a subject's body, to improve predictive capabilities, based on data accumulated at short intervals or from past and near-present durations.

These and other aspects of the disclosed subject matter, as well as additional novel features, will be apparent from the description provided herein. The intent of this summary is not to be a comprehensive description of the subject matter, but rather to provide a short overview of some of the subject matter's functionality. Other systems, methods, features and advantages herein provided will become apparent to one with skill in the art upon examination of the accompanying Figures and detailed description. It is intended that all such additional systems, methods, features and advantages that are included within this description, be within the scope of any claims filed with this disclosure or with a subsequent disclosure.

BRIEF DESCRIPTION OF FIGURE OF THE DRAWINGS

The novel features believed characteristic of the disclosed subject matter will be set forth in claims. The disclosed subject matter itself, however, as well as a preferred mode of use, further objectives, and advantages thereof, will best be understood by reference to the following detailed description of an illustrative embodiment when read in conjunction with the accompanying drawings.

FIG. 8 depicts a representative sample of a system having direct wireless functional connectivity between a subject and a mobile device.

DETAILED DESCRIPTION OF THE INVENTION

Figure 1:
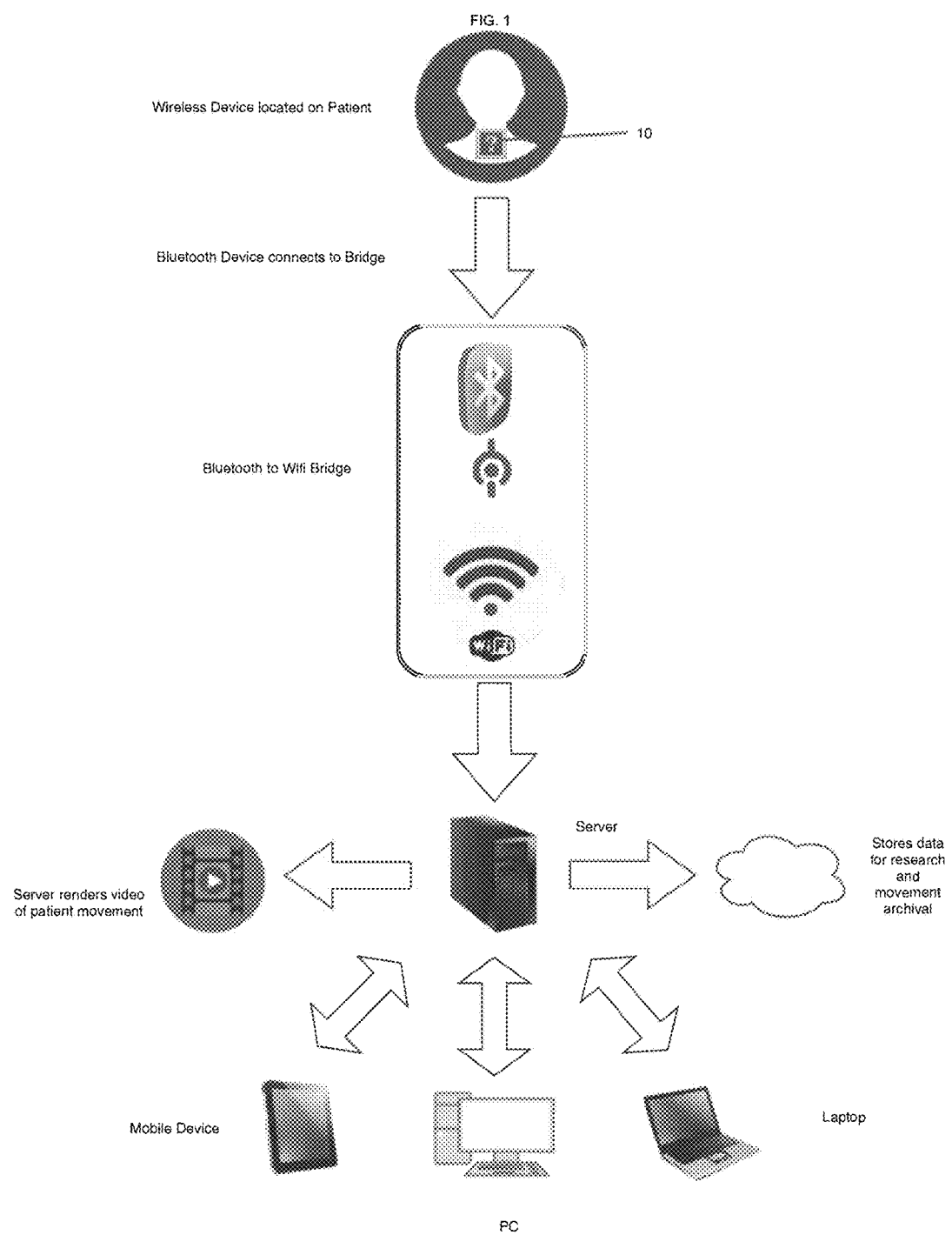
FIG. 1 depicts a schematic view of a representative sample of one embodiment of the system disclosed herein.

The terminology used herein is for the purpose of describing particular embodiments only, and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

For the sake of simplicity and to give the claims of this patent application the broadest interpretation and construction possible, the conjunctive "and" may also be taken to include the disjunctive "or," and vice versa, whenever necessary to give the claims of this patent application the broadest interpretation and construction possible. Likewise, when the plural form is used, it may be taken to include the singular form, and vice versa.

It will be understood that, although the terms first, second, third, etc. may be used herein to describe various elements, these elements should not be limited by these terms. These terms are only used to distinguish one element from another element.

The disclosure herein is not limited by construction material(s) to the extent that such materials satisfy the structural and/or functional requirements. Similarly, the disclosure herein is not limited to the particular combination and/or arrangement of components or functional units of the system, to the extent that the same or comparable functionality may be achieved using a different combination and/or arrangement of components or functional units. For example, there can be more than one physical server, depending on the need for processing power and storage. A system serving a relatively small number of subjects may only require one physical server unit to perform all of the necessary system functions, whereas a system serving a relatively large number of subjects (or serving a facility having a number of separate and/or dispersed administrative units needing servicing) may require a number of servers. Moreover, some multi-server systems may include separate servers serving different functions, whereas some multi-server systems may include servers which each independently provide all functionalities needed for the subjects associated with such server. Furthermore, server functionality may be accomplished by any processor in some circumstances.

The disclosed system includes computer programming that uses yaw, pitch and roll data sensed from a patient, to move a 3D representation of a patient on the screen of a monitor and/or mobile device. The application also utilizes a subset of that data to perform calculations in the background, to alert a caregiver to the potential for a patient fall or other incident monitored for the subject. The acceleration data is what is used to perform such predictive analytics. The data is rendered in real time for system alarming purposes, and it is also stored long term to reevaluate events if desired; the application can be opened, then an interval or time frame chosen for re-sensing, then the data and associated coordinates replay the event.

The sensing device (10) of the system comprises (includes) a 3-axis accelerometer, sensing data concerning the subject's x, y and z axes. More preferably, the sensing device includes a 3-dimensional 3-axis gyroscope and accelerometer (sometimes referred to as a 6-axis accelerometer and gyroscope) that also includes the functionality of Bluetooth low energy version 4.1. The disclosed system may also utilize firmware that extracts yaw, pitch, and roll from the device, then sends the data in packets to receiving devices. In a preferred embodiment, the packets contain up to approximately 20 bytes. Ideally each packet is configured to contain ax, ay, az, gx, gy, and gz coordinates (or combinations thereof) from the accelerometer, and a timestamp for reordering the packets in the application, to ensure processing occurs in the correct order. The processor may apply any one or more of a variety of filtering algorithms, such as (for example) Kalman, Madgwick, or Mahony filtering to achieve the accelerometer stability necessary to extract yaw, pitch, and roll, for translating the orientation of the 3D model (such as, for example, a torso mannequin). The discloses system then uses the ax, ay, and az positioning values for the predictive calculation. In one embodiment, the processor compares the minimum and maximum values in arrays of ax, ay and az values. In another embodiment, the two most recent values in each array are compared; in other embodiments, each of the most recent values in each array may be compared to more than just the respective penultimate value in that array. In yet another embodiment, one or more of the three values may be weighted. The processor then uses the differentials for the predictive calculation.

Ideally, the system uses a User Datagram Protocol instead of Transmission Control Protocol, for the most efficient transmission of the packet. Although UDP does not require an acknowledgment that the packet was received, the disclosed system uses the timestamp on the rendering server or processor to make sure the packet is processed in the correct order.

The disclosed system can utilize data from a wide variety of 3, 6 or 9 axis accelerometers, and can receive data via a wide variety of protocols such as wired ethernet, wifi, or a 2.0 Bluetooth. Accordingly, the system is agnostic to (accepts data produced by) any device that can send data at a less than 30 ms interval, thereby allowing the application to collect data with high frequency to produce the model, and effectively apply the predictive algorithm with enough lead time to anticipate undesirable incidents.

Ideally the disclosed system is a totally wireless solution, but not necessarily. Ideally, the accelerometer device may be battery powered, and encased in a droplet resistant antimicrobial case that can be wiped with health grade sanitizing wipes.

The system is capable of a number of different communications configurations. For wifi, if the accelerometer is coupled with a wifi enabled device, there is no need for a Bluetooth bridge. The location must have adequate wifi coverage in the network. The device attached to the subject would be assigned an IP address. Then it would communicate directly with the system server to deliver the packets to the processing unit and its software programming.

For devices utilizing an accelerometer coupled or integrated with a Bluetooth enabled chip or device, there is another option of direct-to-device communication. This configuration will allow monitoring of a subject via smart phone, personal computer, laptop, or tablet within the Bluetooth low energy device's acceptable range around the sensors. In some circumstances, that range is approximately 33 feet. Any device running the disclosed application, and having Bluetooth 4.0 (or above) capability, can connect the subject sensing device to a nearby monitor. This may allow the Bluetooth enabled accelerometer to stream data directly to the device, allowing the connected device to render the 3D model and process the stream with no need for a server.

Another configuration utilizing an accelerometer coupled/integrated with a Bluetooth chip or device may require a bridge to communicate with the server of the disclosed system. Preferably the bridge is a device that is both Bluetooth low-energy dual-mode ready, and wifi or ethernet enabled. The Bluetooth dual mode side can act as an iBeacon (Bluetooth LE, or BLE) receiver. There is a small transport script that is written, enabling the processor to read each incoming packet, then directs the packet to the wifi or ethernet enabled side for transmission to the rendering server or processor. Again, the disclosed system sends data using UDP to ensure the fastest possible transactions occur. Each of the bridge devices have the capability to communicate with up to seven devices concurrently. As the connection signal weakens, the accelerometer device typically will automatically connect to the strongest signal in range.

Figure 5:
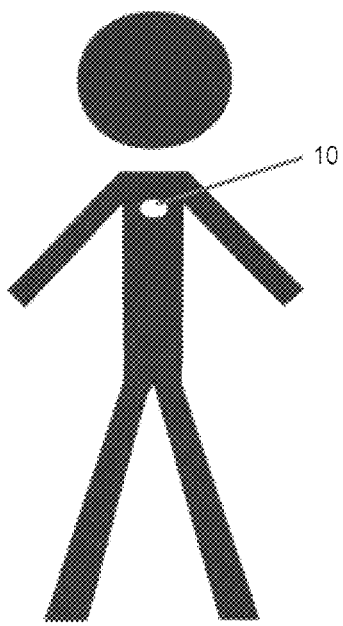
FIG. 5 depicts the placement of a sensor on a subject.

The location of the sensor device on the patient may enhance the gathering of accurate data. Ideally, there are two optimal location possibilities, for the most effective gathering of patient data—a centrally located sensor unit (such as FIG. 5), or multiple sensor units placed in key locations over the body. For a single unit on a human subject, it may be that locating the accelerometer device in the center of the patient's chest (on the sternum) is the most effective. This location allows for easy access for caregivers, and has proven to be the most accurate in predicting movement.

Figure 6:
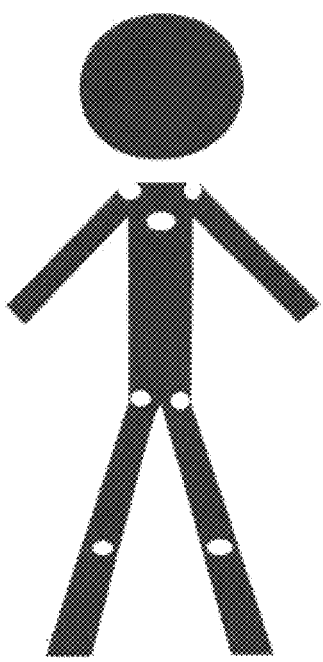
FIG. 6 depicts the placement of seven sensors on a subject.
Figure 7:
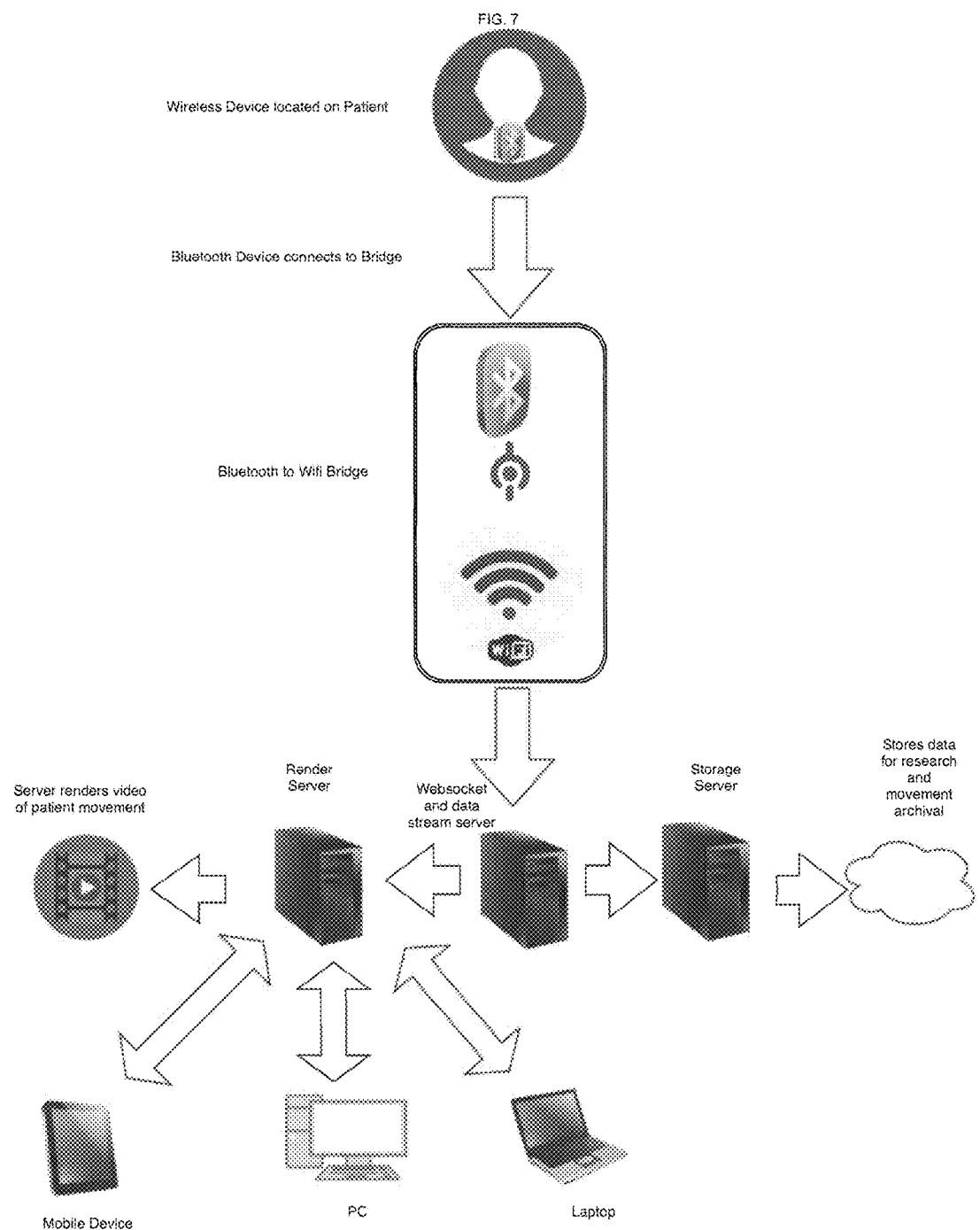
FIG. 7 depicts a representative sample of a system having a plurality of servers and a plurality of monitor screens.

Another configuration involves multiple sensor units. One preferred configuration includes approximately seven sensor devices. (FIG. 6) Placing sensors directly below each knee, on each hip, on each shoulder, and on the sternum is effective in accurately monitoring patient positioning. Each of the sensor devices send data to the processing assembly, that then processes the timestamped data to determine collective displacement to trigger an alarm.

In one embodiment of the system disclosed herein, the 3D model (mannequin) is constructed using Microsoft Direct 3D 11 and/or OpenGL. The renderer is written in C++ and can utilize graphics acceleration for both the real time rendering, and generating the "replay" files to change the orientation of the mannequin based on the most recent positioning data. Multiple threads may be utilized to render multiple patient body orientations in quantities as large as hardware performance will allow.

Figure 2:
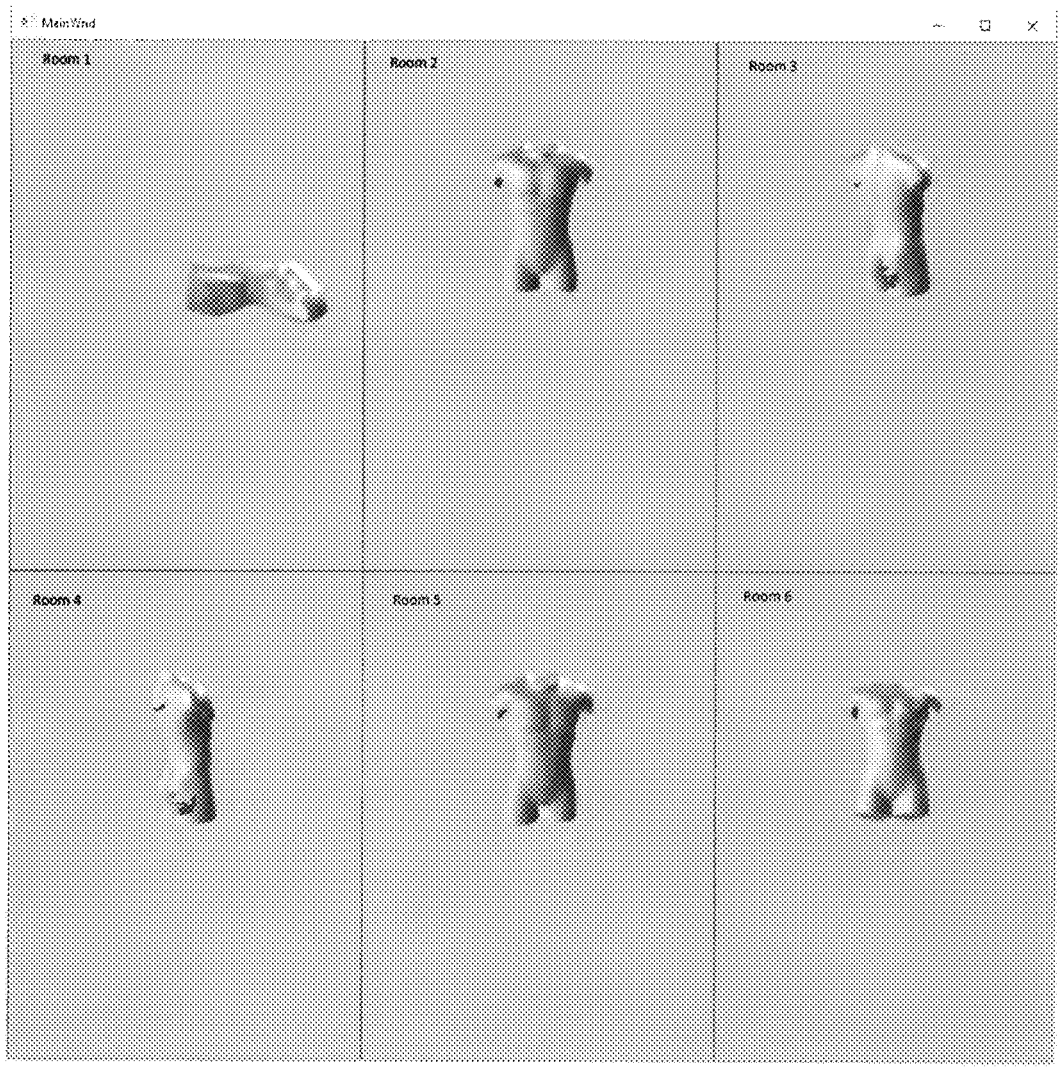
FIG. 2 depicts a representative sample of a monitor screen view showing six torso mannequins of six different subjects.

The application of the disclosed system uses the information stored on the server or processor to then render out to any satellite devices. Typically, each monitor may display the mannequin of up to six different patients (FIG. 2), and the system may serve as many monitors as the chosen hardware will allow.

Figure 3:
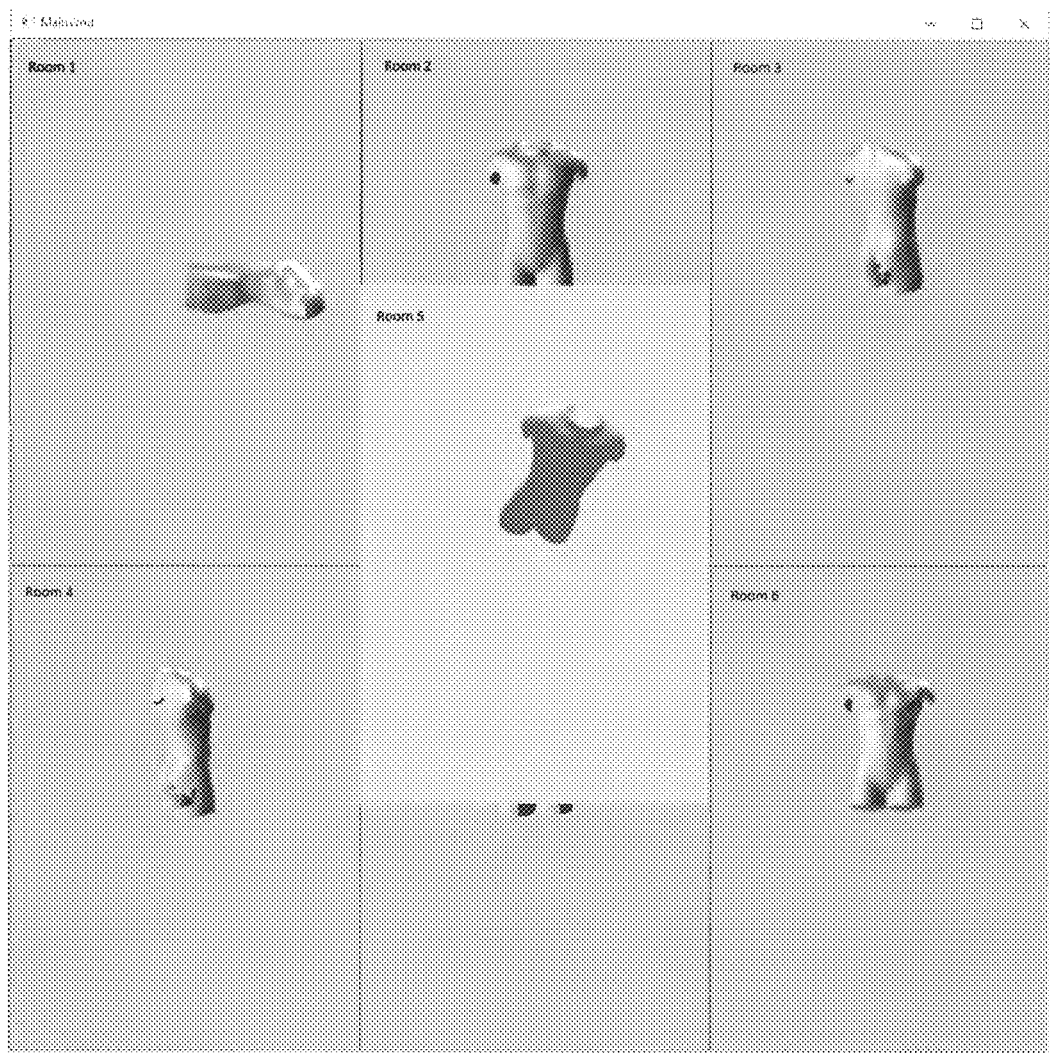
FIG. 3 depicts the view of FIG. 2, with the screen portion of one mannequin warning of imminent fall.

The system may be pre-set with a fall risk level based on the institution's associated scale, and other variables such as the timing and nature of the warning(s) evoked when the fall threshold has been exceeded. Otherwise, the assistant(s) may be prompted by the application to select the desired fall risk threshold and warning options. The software will then alarm the assistant(s) audibly and/or visually and/or vibrationally, when a subject has met or exceeded the accepted threshold of positioning differential parameters (x, y or z). The model of the subject's mannequin may be displayed in different hues (FIG. 3), to depict warning and danger levels to allow the assistant(s) sufficient time to intervene prior to the patient fall.

Upon opening, the application communicates with the server to find all subject sensing devices and monitors that are available on the network. If not already set, the application then populates a dropdown list with subject sensing device names that the assistant(s) can choose to associate with an applicable mannequin portion of one or more monitors. Once associated, the 3D model will orient to the current position of the subject, and the sensor device will begin sensing the subject's 3-axis positioning, sequentially at the selected interval(s), and sequentially sending the packets of positioning data to the processing assembly.

Ideally the system may be deployed for a number of patients, preferably located in proximity to the caregiver(s). For example, a site such as a nursing station may be configured with displays mounted on the wall, at least one each patient being monitored. There typically will be a central workstation located in a central location, but it is not necessary as long as each patient's model appears on at least a portion of a screen being monitored. For example, three satellite monitors, hung in strategic locations between the patients/rooms that are being monitored, may be connected back to the central workstation. Once the caregiver associates the accelerometer device(s) to the patient, the display will begin to demonstrate (and reflect) the patient's movement in bodily positioning.

Although a number of formulas and calculations may be used to analyze the subject-positioning sensor data, one manner used by a preferred embodiment of the disclosed system is to use a custom modified displacement calculation, to utilize past movement to predict future movement. A subject's bodily positioning may be measured by his/her bodily displacement which, for this embodiment of the disclosed system, equals the absolute value of the initial velocity of the subject's body, plus the final velocity, divided by two, all multiplied by the amount of time transpiring between sensing the most recent and the immediately preceding (penultimate) 1 velocities. Applicable formulas for this preferred embodiment include:

Gyro x value: $dx_n = |((V_i+V_f)/2) \times t|$
Gyro y value: $dy_n = |((V_i+V_f)/2) \times t|$
Gyro z value: $dz_n = |((V_i+V_f)/2) \times t|$
$d_n$=displacement
$V_i$=initial velocity
$V_f$=final velocity
t=time interval The system's processing unit applies the respective formula to each respective axis velocity reading coming from the gyroscope, to calculate an axis-specific displacement value for each respective sensor reading.

The system's program also uses those displacement values to populate one of three arrays, one each to accommodate the displacement values from each respective axis into a distinct array. Ideally, each respective array holds data generated as follows:

$Ax = \{dx_0, dx_1, dx_2, dx_3, dx_n \ldots\}$
$Ay = \{dy_0, dy_1, dy_2, dy_3, dy_n \ldots\}$
$Az = \{dz_0, dz_1, dz_2, dz_3, dz_n \ldots\}$ The program then calculates the differential between related data points in the respective array, as follows.

$\%\Delta Ax = (Max\Delta Ax - Min\Delta Ax)/Min\Delta Ax$
$\%\Delta Ay = (Max\Delta Ay - Min\Delta Ay)/Min\Delta Ay$
$\%\Delta Az = (Max\Delta Az - Min\Delta Az)/Min\Delta Az$ To find the difference (delta) in each array, the program takes the largest value minus the smallest value, then divides by the smallest value to get the percent change. Then the program compares that difference to the threshold that has been established by the assistant (depending upon the particular rating system that is used by the system used by the assistant); sometimes it may be necessary to convert rating system's threshold to a percentage too. Reliance upon percentage of change of differential allows comparison with comparable values of the particular rating system involved, essentially normalizing or reconciling both systems. If the differential of any of the differential arrays is equal to or larger than the established threshold, the program will activate the alarm(s). For example, the system will activate an audible alert and/or display a flashing notice on the monitoring device. In this embodiment, the alarm is activated if the maximum $\Delta Ax \geq i$, or the maximum $\Delta Ay \geq i$, or the maximum $\Delta Az \geq i$ (where A is the array and i is the established alarm threshold). In another embodiment with appropriate programming, the application will activate the alarm(s) if the aggregate of all differentials of the differential arrays is larger than an applicable established threshold. Preferably, when the alarm threshold is equaled or exceeded, at least one monitor screen will highlight that subject, and create an audible alarm to alert the assistant(s).

Through the use of displacement differential percentages, the disclosed system is considered to be "agnostic" to fall-rating systems or protocols; it can be deployed in a number of environments, each using a different system of rating or ranking a subject's fall risk. In any such environment, the alarm threshold may be a percentage conversion of the differential, from the scale used by the fall risk rating protocol in the environment. As an example using of a 1-10 fall risk rating scale, a 1 would translate to being a 10% differential, a 2 would translate to a 20% differential, and so on. For a fall risk rating protocol using an ABC scale, an A rating would translate to a 33% differential threshold, and a B rating would translate to a 66% differential threshold.

Figure 4:
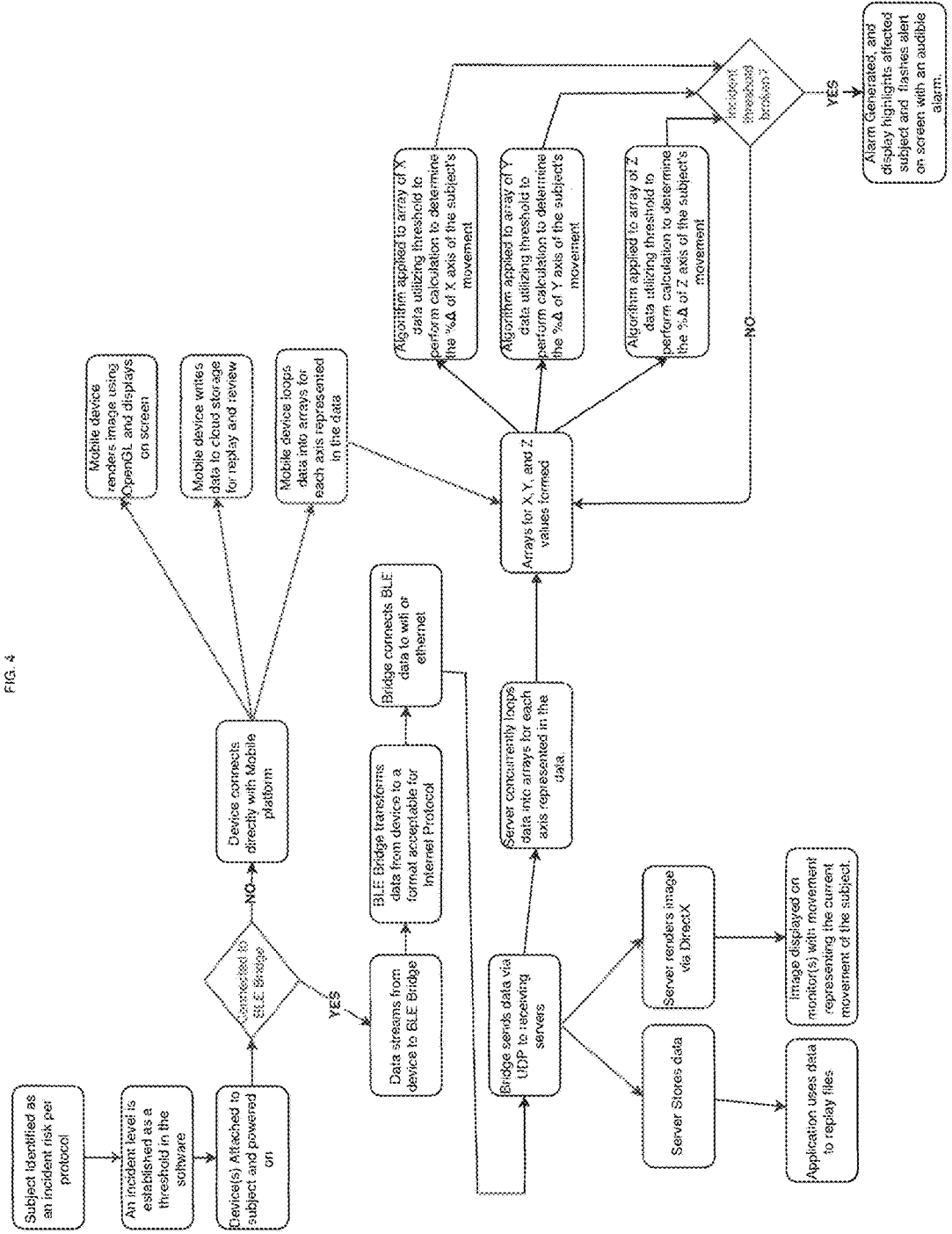
FIG. 4 depicts a logic flow schematic showing the processing steps of the system.

Reference now should be made to the drawings, in which the same reference numbers are used throughout the different figures to designate the same components. FIG. 4 depicts a logic flow schematic showing the processing steps of the system, such as:

(a) at time T1 (promptly after calibrating the sensor with the subject and processor, pairing the sensor and the processor, and posting the subject's mannequin on at least a portion of at least one monitor screen), transmitting the subject's initial x, y and z axis positioning data to the processor, and translating that data to orient the subject's mannequin on at least one monitor screen;

(b) at time T2, sense the subjects x, y, and z axis positioning data, and transmit it to the processor to translate it to re-orient the subject's mannequin, and to analyze the differential between the immediately preceding data to determine whether a fall-risk threshold has been crossed; and (c) if such threshold has been met or crossed, transmit the alert(s) such as highlighting that subject's screen portion, moving the model to the center of the screen, changing the color of the background or model, and/or activating an audible alarm identifying that subject as being at risk of imminent fall.

In general, the invention disclosed herein includes (comprises) a system for predicting the fall of a subject's body, including:

(a) a sensor assembly including a sensor positioned on the subject's body to sequentially sense the subject's spatial positioning at short intervals and generate a corresponding sequence of positioning data, operatively coupled to;

(b) a processing assembly sequentially receiving the positioning data and including a computer processing unit having associated software programming for determining whether the difference between the subject's present positioning and the subject's previous positioning exceeds a threshold predictive of imminent bodily fall, operatively coupled to;

(c) a monitoring assembly including at least one monitor screen showing a representation reflecting the positioning of at least one subject's body according to the current positioning data.

The sensor assembly may further include a 3-axis accelerometer, sensing the subject's positioning relative to the x axis, y axis and z axis. Preferably it may include a 3-dimensional 3-axis gyroscope and accelerometer.

The operative coupling to the processing assembly, from the sensor assembly and/or the monitoring assembly, may include any form of wireless coupling technology.

The sensor sampling intervals may be of any duration needed to obtain accurate 3-axis displacement values, yet short enough to facilitate near-real-time monitoring. For example, the interval(s) may be in the range of between about 0.001 second and 0.03 second, with the interval preferably being about 0.015 second.

The processing assembly should activate at least one imminent-fall or imminent-incident alarm if the subject's displacement differential of any of the differential arrays is equal to or larger than the established threshold.

The representation of the subject's body may appear as a torso mannequin, or similar item mimicking the appearance of a human form. The representation should include a model that does not show any personal health information of the subject's body, or otherwise result in invasion of privacy of the subject when shown on a monitor screen that may not be completely private. The representation or model should not cause any non-compliance with regulations such as the Health Insurance Portability and Accountability Act (HIPAA).

One specific embodiment of the invention disclosed herein is a system for predicting the fall of a subject's body, including:

(a) a sensor assembly including a 3-dimensional 3-axis gyroscope and accelerometer positioned centrally on the subject's body to sense the subject's spatial positioning at intervals of about 0.015 second and generate a corresponding sequence of positioning data, and a battery powered wireless transmitter for sending the positioning data immediately upon each sensing;

(b) a processing assembly including a transceiver for sequentially receiving the positioning data, and a computer processing unit having associated software programming residing thereon for determining whether the displacement differential between the subject's present positioning and the subject's previous positioning exceeds a threshold predictive of imminent bodily fall, accomplished by comparing the subject's displacement differentials of each axis' sequential positioning data obtained after each of the intervals, the displacement differentials of each axis' sequential positioning data calculated from positioning data points including of:

(1) Gyro x value: $dxn=|((Vi+Vf)/2) \times t|$;
(2) Gyro y value: $dyn=|((Vi+Vf)/2) \times t|$; and
(3) Gyro z value: $dzn=|((Vi+Vf)/2) \times t|$, where dn=displacement, Vi=initial velocity, Vf=final velocity, and t=time interval;
(4) each of the positioning data points for each respective axis populating a respective array where $Ax=\{dx0, dx1, dx2, dx3, dxn \ldots\}$, $Ay=\{dy0, dy1, dy2, dy3, dyn \ldots\}$, and $Az=\{dz0, dz1, dz2, dz3, dzn \ldots\}$;
(5) the displacement differentials of each axis' sequential positioning data calculated as % $\Delta Ax = (Max\Delta Ax - Min\Delta Ax)/Min\Delta Ax$, % $\Delta Ay = (Max\Delta Ay - Min\Delta Ay)/Min\Delta Ay$, and % $\Delta Az = (Max\Delta Az - Min\Delta Az)/Min\Delta Az$, yielding the percentage of change of body position for the subject for the respective axis; and (c) a monitoring assembly including a plurality of monitor screens, each showing a representation reflecting the positioning of at least one of a plurality of subject's bodies according to the current positioning data for the respective subject, the processing assembly activating at least one imminent-fall or imminent-incident alarm if the displacement differential of any of the arrays is equal to or larger than an established threshold, the alarm selected from the group consisting of visual, auditory or tactile stimulation or combinations thereof.

The monitoring assembly may further include a centralized plurality of monitor screens, each independently displaying and monitoring up to six representations for different subjects, and a plurality of satellite monitor screens in proximity to the respective subjects monitored thereon. The plurality of satellite monitor screens may also including mobile electronic devices operatively coupled to the processing assembly.

Besides the system described herein, the invention includes the method of method of predicting and monitoring the fall of a subject's body using a system of claim 2, comprising the steps of:

(a) establishing a fall-risk threshold on the processing assembly;
(b) situating the sensor assembly on a subject whose fall risk will be monitored on a monitor screen; and
(c) activating the processing assembly and sensor assembly and monitoring assembly, to allow the operative coupling of the processing assembly with the sensor assembly and the monitor assembly, and to initiate the sequential sensing of the subject's bodily positioning displacement to be displayed on a monitor screen.

We claim:

1. A system for predicting the fall of a subject's body, comprising:

(a) a sensor assembly comprising a sensor positioned on the subject's body to sequentially sense the subject's spatial positioning at intervals in the range of between about 0.001 second and 0.03 second and generate a corresponding sequence of positioning data, operatively coupled to;

(b) a processing assembly sequentially receiving said positioning data and comprising a computer processing unit having associated software programming for determining whether the difference between the subject's present positioning and the subject's previous positioning exceeds a threshold predictive of an imminent incident.

2. A system of claim 1, further comprising, operatively coupled to said processing assembly, a monitoring assembly comprising at least one monitor screen showing a representation reflecting the positioning of at least one subject's body according to the current positioning data.

3. A system of claim 2, said sensor assembly further comprising a sensor assembly comprising a 3-axis accelerometer sensing the subject's positioning relative to the x axis, y axis and z axis.

4. A system of claim 2, said sensor assembly further comprising a sensor assembly comprising a 3-dimensional 3-axis gyroscope and accelerometer.

5. A system of claim 2, said operative coupling to said processing assembly comprising wireless coupling.

6. A system of claim 1, said interval being 0.015 second.

7. A system of claim 3, said computer processing unit and associated software programming's determining whether the difference between the subject's present positioning and the subject's previous positioning exceeds a threshold predictive of an imminent incident is accomplished by comparing the subject's displacement differentials of each axis' sequential positioning data obtained after each of said intervals.

8. A system of claim 7, said displacement differentials of each axis' sequential positioning data calculated from positioning data points comprising:
(a) x axis value: $dxn=|((Vi+Vf)/2) \times t|$;
(b) y axis value: $dyn=|((Vi+Vf)/2) \times t|$; and
(c) z axis value: $dzn=|((Vi+Vf)/2) \times t|$;
where dn=displacement, Vi=initial velocity, Vf=final velocity, and t=time interval.

9. A system of claim 8, each of said positioning data points for each respective axis populating a respective array where Ax={dx0, dx1, dx2, dx3, dxn . . . }, Ay={dy0, dy1, dy2, dy3, dyn . . . }, and Az={dz0, dz1, dz2, dz3, dzn . . . }.

10. A system of claim 9, said displacement differentials of each axis' sequential positioning data calculated as %ΔAx=(MaxΔAx−MinΔAx)/MinΔAx, %ΔAy=(MaxΔAy−MinΔAy)/MinΔAy, and %ΔAz=(MaxΔAz−MinΔAz)/MinΔAz, yielding the percentage of change of body position for the subject for the respective axis.

11. A system of claim 10, said processing assembly activating at least one imminent-incident alarm if the differential of any of the differential arrays is equal to or larger than the established threshold.

12. A system of claim 2, said representation comprising a torso mannequin.

13. A system of claim 2, said representation comprising a model not showing any personal health information of the subject's body.

14. A system of claim 1, further comprising a monitoring assembly comprising a plurality of monitor screens, each showing a representation reflecting the positioning of at least one of a plurality of subject's bodies according to the current positioning data for the respective subject.

15. A system of claim 1, said threshold predictive of imminent bodily fall derived from a third-party fall-risk rating system.

16. A system of claim 15, further comprising a warning means for warning an interested third party that the subject is at risk of imminent bodily fall.

17. A system for predicting the fall of a subject's body, comprising:
(a) a sensor assembly comprising a 3-dimensional 3-axis gyroscope and accelerometer positioned centrally on the subject's body to sense the subject's spatial positioning at intervals of 0.015 second and generate a corresponding sequence of positioning data, and a battery powered wireless transmitter for sending said positioning data immediately upon each sensing;
(b) a processing assembly comprising a transceiver for sequentially receiving said positioning data, and a computer processing unit having associated software programming residing thereon for determining whether the displacement differential between the subject's present positioning and the subject's previous positioning exceeds a threshold predictive of imminent bodily fall, accomplished by comparing the subject's displacement differentials of each axis' sequential positioning data obtained after each of said intervals, said displacement differentials of each axis' sequential positioning data calculated from positioning data points comprising:
(1) x axis value: $dxn=|((Vi+Vf)/2) \times t|$;
(2) y axis value: $dyn=|((Vi+Vf)/2) \times t|$; and
(3) z axis value: $dzn=|((Vi+Vf)/2) \times t|$ where dn=displacement, Vi=initial velocity, Vf=final velocity, and t=time interval; each of said positioning data points for each respective axis populating a respective array where Ax={dx0, dx1, dx2, dx3, dxn . . . }, Ay={dy0, dy1, dy2, dy3, dyn . . . }, and Az={dz0, dz1, dz2, dz3, dzn . . . }, said displacement differentials of each axis' sequential positioning data calculated as %ΔAx=(MaxΔAx−MinΔAx)/MinΔAx, %ΔAy=(MaxΔAy−MinΔAy)/MinΔAy, and %ΔAz=(MaxΔAz−MinΔAz)/MinΔAz, yielding the percentage of change of body position for the subject for the respective axis; and
(c) a monitoring assembly comprising a plurality of monitor screens, each showing a representation reflecting the positioning of at least one of a plurality of subject's bodies according to the current positioning data for the respective subject, said processing assembly activating at least one imminent-fall alarm if the displacement differential of any of the arrays is equal to or larger than an established threshold, said alarm selected from the group consisting of visual, auditory or tactile stimulation or combinations thereof.

18. A system of claim 17, said monitoring assembly further comprising a centralized plurality of monitor screens, each independently displaying and monitoring up to six representations for different subjects, and a plurality of satellite monitor screens in proximity to the respective subjects monitored thereon.

19. A system of claim 18, said plurality of satellite monitor screens including mobile electronic devices operatively coupled to said processing assembly.

20. A method of predicting and monitoring the fall of a subject's body using a system of claim 2, comprising the steps of:
(a) establishing a fall-risk threshold on the processing assembly;
(b) situating the sensor assembly on a subject whose fall risk will be monitored on a monitor screen; and
(c) activating the processing assembly and sensor assembly and monitoring assembly, to allow the operative coupling of the processing assembly with the sensor assembly and the monitor assembly, and to initiate the sequential sensing of the subject's bodily positioning displacement to be displayed on a monitor screen.

* * * * *